United States Patent
Slyusarenko et al.

(10) Patent No.: US 11,730,380 B2
(45) Date of Patent: Aug. 22, 2023

(54) ELECTRONIC DEVICE AND METHOD FOR MONITORING BLOOD PRESSURE

(71) Applicant: Samsung Electronics Co., Ltd., Suwon-si (KR)

(72) Inventors: Kostyantyn Slyusarenko, Suwon-si (KR); Andrii Omelchenko, Suwon-si (KR); Stanislav Prykhodko, Suwon-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 212 days.

(21) Appl. No.: 17/114,877

(22) Filed: Dec. 8, 2020

(65) Prior Publication Data
US 2021/0196137 A1  Jul. 1, 2021

(30) Foreign Application Priority Data
Dec. 26, 2019  (KR) .......................... 10-2019-0174801

(51) Int. Cl.
*A61B 5/021* (2006.01)
*A61B 5/00* (2006.01)
*A61B 5/024* (2006.01)

(52) U.S. Cl.
CPC .......... *A61B 5/02125* (2013.01); *A61B 5/681* (2013.01); *A61B 5/6803* (2013.01); *A61B 5/6804* (2013.01); *A61B 5/024* (2013.01)

(58) Field of Classification Search
None
See application file for complete search history.

(56) References Cited

U.S. PATENT DOCUMENTS

| | | | |
|---|---|---|---|
| 4,296,754 A | 10/1981 | Hennig et al. | |
| 2004/0030261 A1* | 2/2004 | Rantala ................ | A61B 5/0285 600/561 |
| 2010/0056880 A1* | 3/2010 | Cho .................... | A61B 5/02438 600/509 |
| 2012/0016246 A1* | 1/2012 | Sandgaard ............. | A61B 5/024 600/481 |

(Continued)

FOREIGN PATENT DOCUMENTS

| CN | 109846464 A | 6/2019 |
|---|---|---|
| KR | 10-2011-0037202 A | 4/2011 |
| KR | 10-2019-0097474 A | 8/2019 |

OTHER PUBLICATIONS

International Search Report dated Mar. 22, 2021, issued in International Application No. PCT/KR2020/017855.

*Primary Examiner* — May A Abouelela
*Assistant Examiner* — Aurelie H Tu
(74) *Attorney, Agent, or Firm* — Jefferson IP Law, LLP

(57) ABSTRACT

An electronic device is provided. The electronic device includes at least two pairs of electrodes, and a processor, wherein the processor may be configured to generate a signal and output the signal by using a first pair of electrodes, measure a voltage response signal by using a second pair of electrodes, detect a differential electrocardiogram from the measured voltage response signal, detect a local impedance cardiogram from the measured voltage response signal, calculate a pulse arrival time by using the detected differential electrocardiogram and local impedance cardiogram, and calculate blood pressure by using the calculated pulse arrival time. It is possible to provide various other embodiments.

20 Claims, 12 Drawing Sheets

(56) References Cited

U.S. PATENT DOCUMENTS

| | | | |
|---|---|---|---|
| 2012/0323106 A1 | 12/2012 | Harrold et al. | |
| 2014/0249434 A1 | 9/2014 | Banet et al. | |
| 2015/0073239 A1* | 3/2015 | Pei | A61B 5/14551 |
| | | | 600/324 |
| 2015/0126820 A1* | 5/2015 | Muhlsteff | A61B 5/742 |
| | | | 600/479 |
| 2016/0174852 A1* | 6/2016 | He | A61B 5/02416 |
| | | | 600/301 |
| 2017/0281024 A1 | 10/2017 | Narasimhan et al. | |
| 2017/0340209 A1 | 11/2017 | Klaassen et al. | |
| 2017/0340219 A1 | 11/2017 | Sullivan et al. | |
| 2018/0085012 A1* | 3/2018 | Wei | A61B 5/0245 |
| 2018/0317784 A1 | 11/2018 | Albert | |
| 2021/0000376 A1 | 1/2021 | Lee et al. | |

\* cited by examiner

ELECTRONIC DEVICE AND METHOD FOR MONITORING BLOOD PRESSURE

CROSS-REFERENCE TO RELATED APPLICATION(S)

This application is based on and claims priority under 35 U.S.C. § 119(a) of a Korean patent application number 10-2019-0174801 filed on Dec. 26, 2019, in the Korean Intellectual Property Office, the disclosure of which is incorporated by reference herein in its entirety.

BACKGROUND

1. Field

The disclosure relates to an electronic device and a method for monitoring blood pressure. More particularly, the disclosure relates to a cuffless sphygmomanometer for measuring blood pressure using electrodes attached to plural locations of the body, such arms, legs, and a region around the heart.

2. Description of Related Art

There are several indicators of the health condition of a person. Among them, blood pressure is an important biological index containing information about cardiac output (the amount of blood expelled from the human heart or ventricle in one minute), vascular compliance, and physiological changes in a patient. The most commonly used sphygmomanometer (or, blood pressure monitor) for measuring blood pressure is a cuffed sphygmomanometer, which applies pressure with the cuff to a region where arterial blood passes to stop the flow of blood and measures systolic blood pressure and diastolic blood pressure while slowly reducing the pressure. However, as the cuffed sphygmomanometer is bulky and inconvenient to carry, it may be unsuitable for continuous real-time monitoring of changes in blood pressure of a person. Hence, in recent years, active research has been conducted on cuffless sphygmomanometers for measuring blood pressure.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an electronic device and a method for monitoring blood pressure.

A cuffless sphygmomanometer may measure blood pressure using electrodes attached to plural locations of the body, such arms, legs, and a region around the heart. It may be difficult to continuously use the method of measuring blood pressure using plural electrodes, and the locations of the attached electrodes can also be important in measuring blood pressure.

A cuffed sphygmomanometer may measure blood pressure in a specific region of the body, but it is difficult to continuously measure blood pressure because pressure is to be applied periodically.

Additional aspects will be set forth in part in the description which follows and, in part, will be apparent from the description, or may be learned by practice of the presented embodiments.

In Accordance with an aspect of the disclosure, an electronic device is provided. The electronic device includes at least two pairs of electrodes, and a processor, wherein the processor may be configured to generate a signal and output the signal by using a first pair of electrodes, measure a voltage response signal by using a second pair of electrodes, detect a differential electrocardiogram from the measured voltage response signal, detect a local impedance cardiogram from the measured voltage response signal, calculate a pulse arrival time by using the detected differential electrocardiogram and local impedance cardiogram, and calculate blood pressure by using the calculated pulse arrival time.

In accordance with another aspect of the disclosure, a method for operating an electronic device is provided. The method includes generating a signal and outputting the signal by using a first pair of electrodes, measuring a voltage response signal by using a second pair of electrodes, detecting a differential electrocardiogram from the measured voltage response signal, detecting a local impedance cardiogram from the measured voltage response signal, calculating a pulse arrival time by using the detected differential electrocardiogram and local impedance cardiogram, and calculating blood pressure by using the calculated pulse arrival time.

According to various embodiments of the disclosure, the electronic device can continuously measure blood pressure using a cuffless scheme.

According to various embodiments of the disclosure, as blood pressure can be measured by placing a pair of electrodes close together, blood pressure measurement can be implemented even with a small electronic device.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features and advantages of certain embodiments of the disclosure will be more apparent from the following description taken in conjunction with the accompanying drawings, in which.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
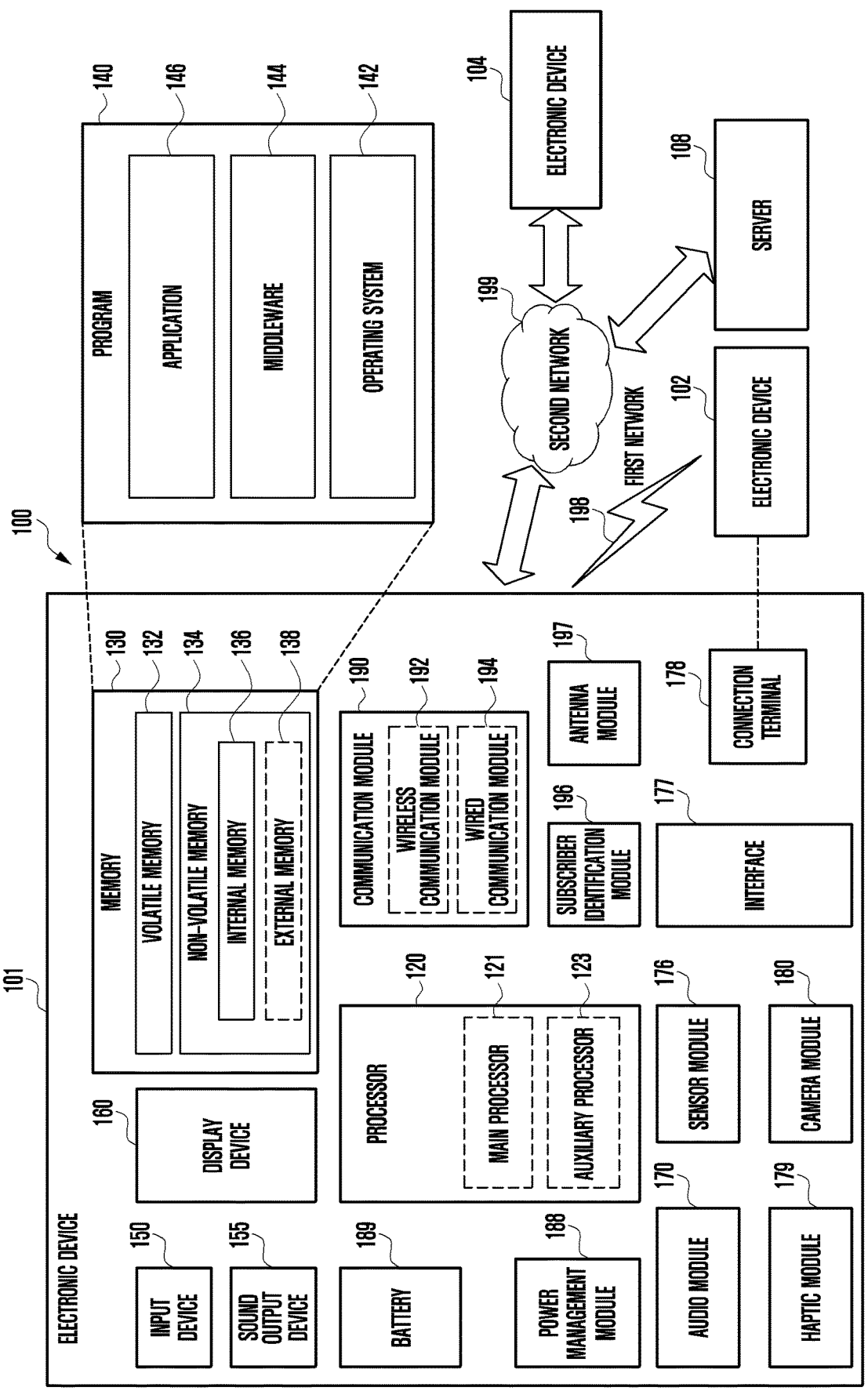
FIG. 1 is a block diagram of an electronic device in a network environment according to an embodiment of the disclosure.

FIG. 1 is a block diagram illustrating an electronic device in a network environment according to an embodiment of the disclosure.

Referring to FIG. 1, an electronic device 101 in a network environment 100 may communicate with an electronic device 102 via a first network 198 (e.g., a short-range wireless communication network), or an electronic device 104 or a server 108 via a second network 199 (e.g., a long-range wireless communication network). According to an embodiment of the disclosure, the electronic device 101 may communicate with the electronic device 104 via the server 108. According to an embodiment of the disclosure, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments of the disclosure, at least one (e.g., the display device 160 or the camera module 180) of the components may be omitted from the electronic device 101, or one or more other components may be added in the electronic device 101. In some embodiments of the disclosure, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment of the disclosure, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment of the disclosure, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., a sleep) state, or together with the main processor 121 while the main processor 121 is in an active state (e.g., executing an application). According to an embodiment of the disclosure, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thererto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment of the disclosure, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment of the disclosure, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment of the disclosure, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment of the disclosure, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment of the disclosure, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment of the disclosure, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment of the disclosure, the haptic module 179 may include, for example, a motor, a piezoelectric element, or an electric stimulator.

The camera module 180 may capture an image or moving images. According to an embodiment of the disclosure, the camera module 180 may include one or more lenses, image sensors, image signal processors, or flashes.

The power management module 188 may manage power supplied to the electronic device 101. According to one embodiment of the disclosure, the power management module 188 may be implemented as at least part of, for example, a power management integrated circuit (PMIC).

The battery 189 may supply power to at least one component of the electronic device 101. According to an embodiment of the disclosure, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment of the disclosure, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The antenna module 197 may transmit or receive a signal or power to or from the outside (e.g., the external electronic device) of the electronic device 101. According to an embodiment of the disclosure, the antenna module 197 may include an antenna including a radiating element composed of a conductive material or a conductive pattern formed in or on a substrate (e.g., a PCB). According to an embodiment of the disclosure, the antenna module 197 may include a plurality of antennas. In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment of the disclosure, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment of the disclosure, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

Figure 2:
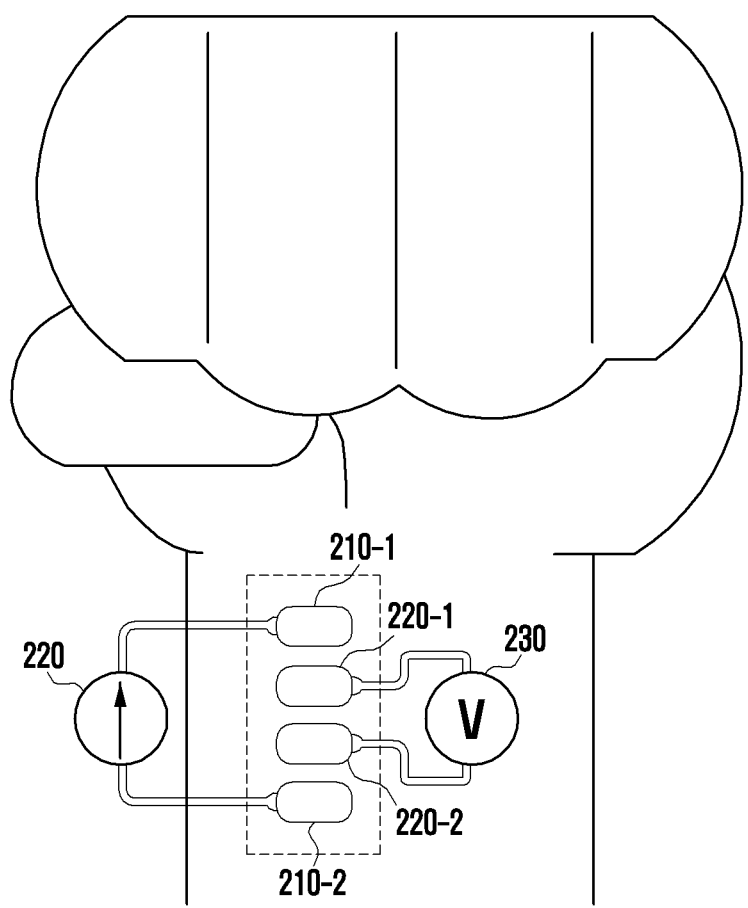
FIG. 2 illustrates a partial configuration of an electronic device according to an embodiment of the disclosure.

FIG. 2 illustrates a partial configuration of an electronic device according to an embodiment of the disclosure.

Referring to FIG. 2, the electronic device (e.g., the electronic device 101 in FIG. 1) according to various embodiments of the disclosure may measure a raw bioelectrical signal from, for example, the wrist. To measure a raw bioelectrical signal, the electronic device 101 may include a signal generation module 220, a plurality of electrodes 210-1, 210-2, 220-1 and 220-2, and a signal measurement module 230 in addition to the configuration shown in FIG. 1. Alternatively, the signal generation module 220, the plural electrodes 210-1, 210-2, 220-1 and 220-2, and the signal measurement module 230 may be configured separately from the electronic device 101 by further including a communication module (not shown) (e.g., the communication module in FIG. 1).

The signal generation module 220 is a module that generates a signal and may generate a current, for example. The generated current may be a current of a relatively high modulation frequency (MF), and the frequency may be, for example, 0 to 10 kilohertz (KHz). The signal generation module 220 may transmit a generated signal to the body by using a pair of electrodes 210-1 and 210-2. For example, the signal generation module 220 may generate a signal to measure an impedance cardiogram (ICG).

The plural electrodes 210-1, 210-2, 220-1 and 220-2 may include at least two pairs of electrodes. The plural electrodes 210-1, 210-2, 220-1 and 220-2 may be attached to the body to measure a body signal or to transmit a generated signal to the body. A first pair of electrodes 210-1 and 210-2 may be connected to the signal generation module 220 to transmit a signal generated by the signal generating module 220 to the body. A second pair of electrodes 220-1 and 220-2 may be connected to the signal measurement module 230 to measure a signal of the body. The plural electrodes 210-1, 210-2, 220-1 and 220-2 may be positioned parallel to or vertically to, for example, an artery. FIG. 2 shows an example where the plural electrodes 210-1, 210-2, 220-1 and 220-2 are positioned vertically to an artery.

The signal measurement module 230 may measure a signal of the body by using a pair of electrodes 220-1 and 220-2. The sampling frequency of the signal measurement module 230 for signal measurement may be higher than the frequency of the signal generated by the signal generation module 220. The signal measurement module 230 may measure a signal with a relatively high sampling frequency, for example, in a range of 100 KHz. The signal measurement module 230 may perform signal measurement at a higher sampling frequency than the frequency of the signal generated by the signal generation module 220.

The signal measurement module 230 may measure a signal of the body in the form of a voltage. In the description, the measured body voltage signal may be referred to as a voltage response signal (VRS).

FIGS. 3A, 3B, 3C, and 3D illustrate electronic devices of different types according to various embodiments of the disclosure.

Figure 3A:
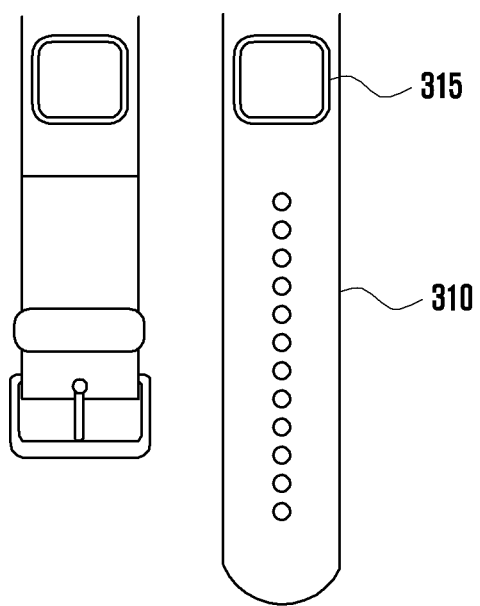
FIGS. 3A, 3B, 3C and 3D illustrate electronic devices of different types according to various embodiments of the disclosure.

Referring to FIG. 3A, illustrates an electronic device that can be attached to the wrist. For example, the electronic device that can be attached to the wrist may be a watch or a wristband. FIG. 3A shows an example in which plural electrodes 315 are disposed on both sides of the watch strap 310, and the electronic device may measure a voltage response signal by using the plural electrodes 315. FIG. 2 may show an example where plural electrodes are disposed on one side of the watch strap, and FIG. 3A may show an example where the plural electrodes 315 are disposed on both sides of the watch strap 310. When the plural electrodes 315 are disposed on both sides of the watch strap 310 as shown in FIG. 3A, the plural electrodes 315 may be disposed parallel to an artery.

Figure 3B:
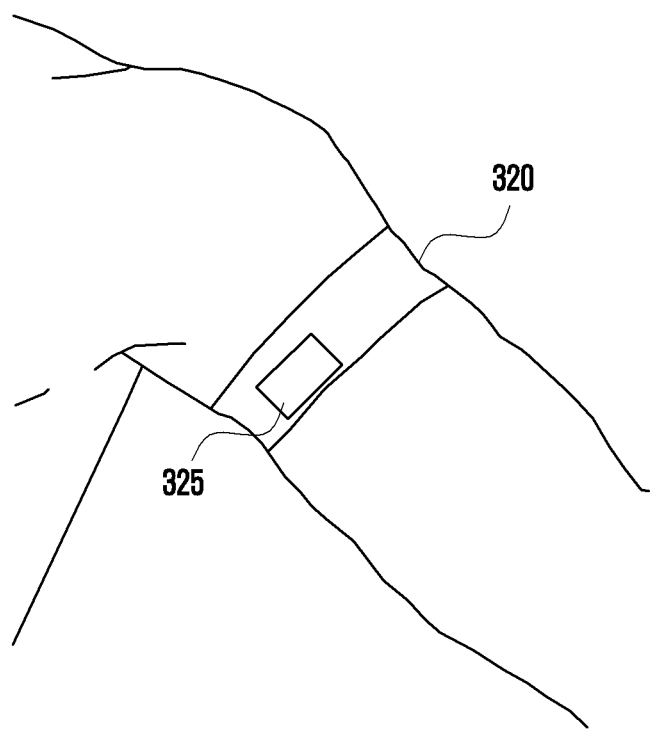

Referring to FIG. 3B, illustrates an electronic device that can be attached to the forearm. The electronic device that can be attached to the forearm may correspond to, for example, an arm band 320. The arm band 320 may include a plurality of electrodes 325.

Figure 3C:
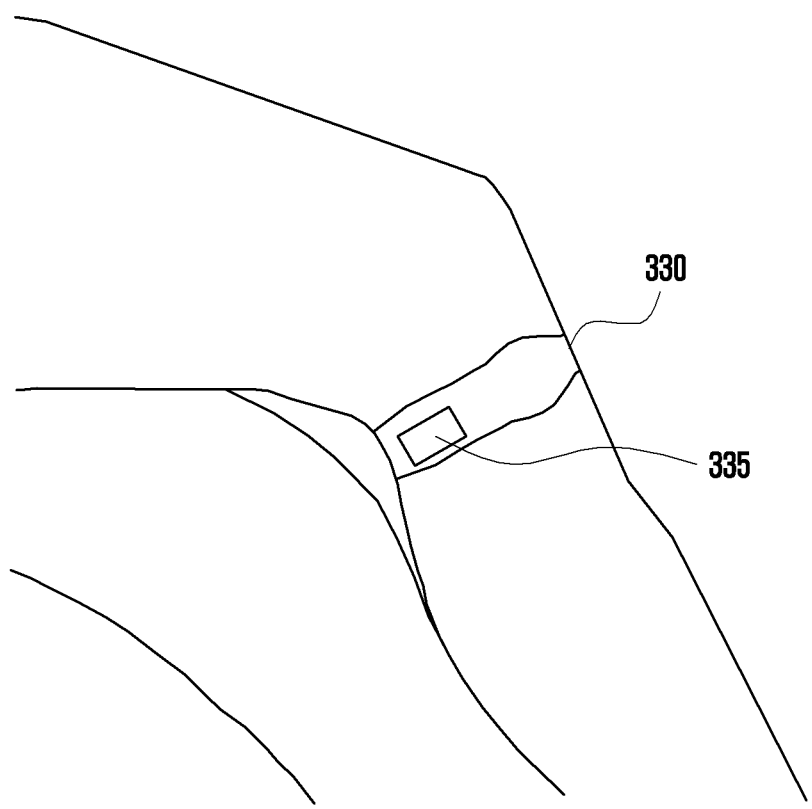

Referring to FIG. 3C, illustrates an electronic device that can be attached to the leg. The electronic device that can be attached to the leg may correspond to, for example, the leg band 330. The leg band 330 may also include a plurality of electrodes 335.

Figure 3D:
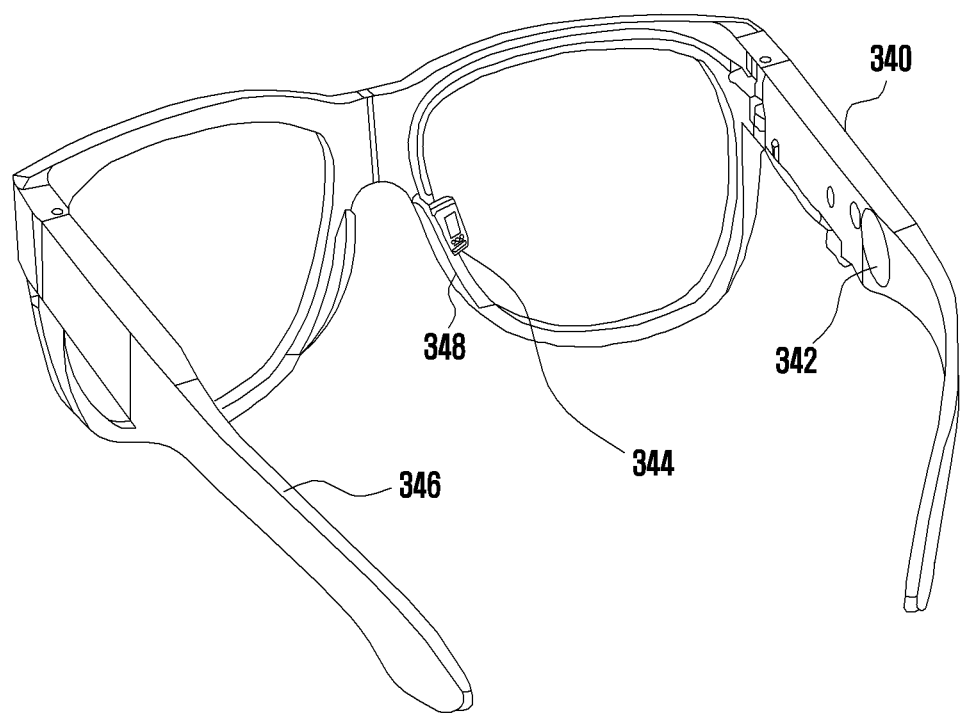

Referring to FIG. 3D, illustrates an electronic device attached to the eyeglasses. For example, in the eyeglasses, the nose arm 348 and the temple 340 may contact the body, so that a plurality of electrodes 342, 344, and 346 may be disposed on the nose aim 348 and the temple 340.

Referring to FIGS. 3A, 3B, 3C, and 3D, the disclosure is described by taking a watch, an arm band, a wrist band, a leg band, and eyeglasses as examples. However, the disclosure may be applied to any electronic device that can be attached to the body and includes a plurality of electrodes, such as rings, necklaces, clothes, or socks.

Figure 4:
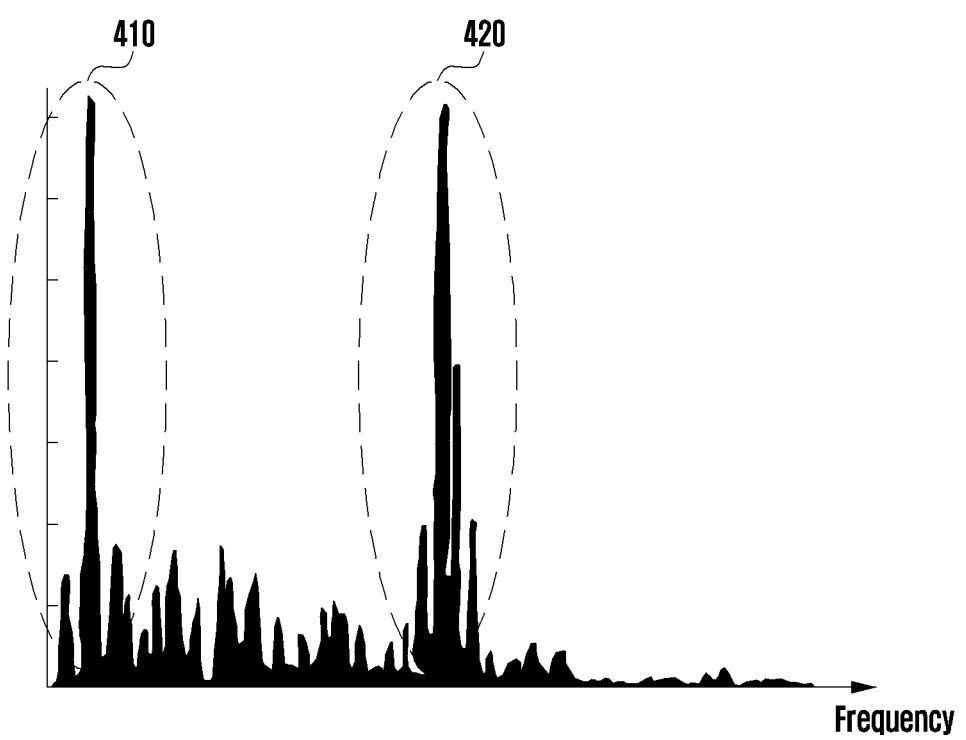
FIGS. 4 and 5 illustrate voltage response signals measured according to various embodiments of the disclosure.
Figure 5:
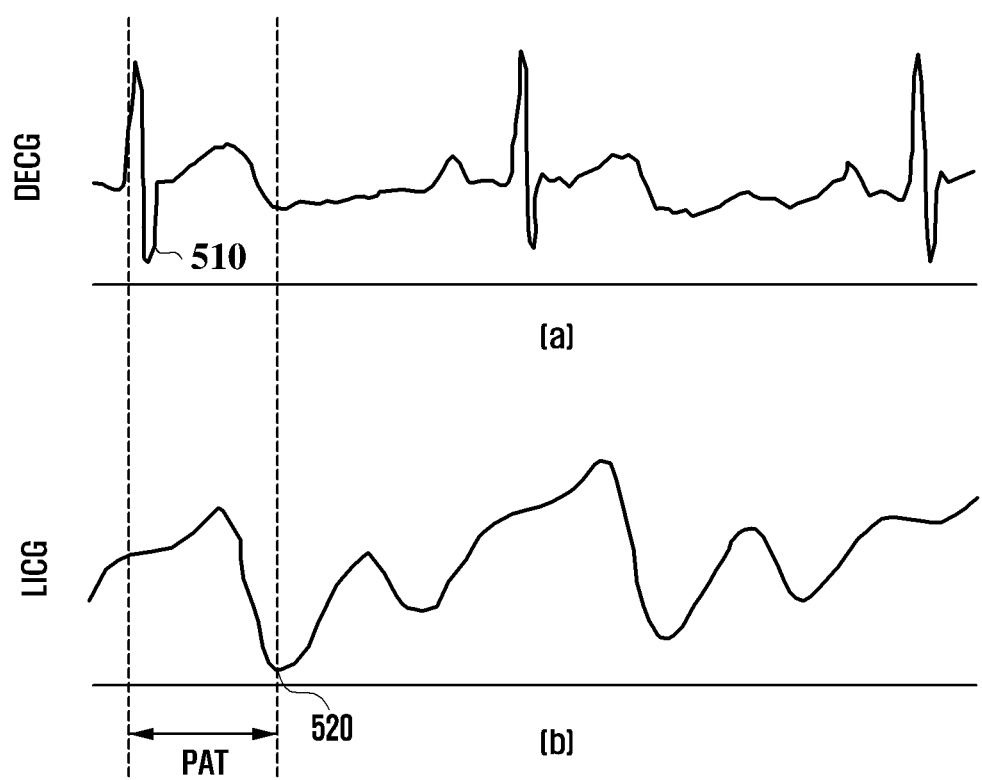

FIGS. 4 and 5 illustrates of voltage response signals measured according to various embodiments of the disclosure.

Specifically, referring to FIG. 4, it illustrates an analysis of frequency components of a measured voltage response signal. The processor (e.g., the processor 120 in FIG. 1) may analyze frequency components of the voltage response signal measured by a signal measurement module (e.g., the signal measurement module 230 in FIG. 2) using a pair of electrodes (e.g., the electrodes 220-1 and 220-2 in FIG. 2).

The frequency components of the voltage response signal may include electrocardiogram (ECG) frequency components and impedance cardiogram (ICG) frequency components. For example, frequency components 410 of the electrocardiogram may be of 0.3 to 35 hertz (Hz), and frequency components 420 of the impedance cardiogram may be similar to the frequency components of the signal generated by the signal generation module 230.

An ECG may correspond to an electrical signal of the heart measured through electrodes attached to plural preset locations on the body. For example, the electrodes may be disposed at six locations including two wrists, two ankles, and chest regions. In the disclosure, electrodes may be disposed in a local region in addition to the locations described above. In the disclosure, to distinguish between an electrocardiogram measured in a large region where plural preset locations are separated and an electrocardiogram measured in a local region, the electrocardiogram measured in a local region may be referred to as a differential ECG (DECG) or may be referred to as an electrocardiogram along with a location where the electrodes are attached. For example, in the case of measuring an electrocardiogram by attaching electrodes to an arm as a local region, it may be referred to as an arm-ECG.

The impedance cardiogram (ICG) may correspond to an electrical impedance of the chest, and may be a measurement of an impedance that changes when a current generated by an external current source is transmitted to the body through plural electrodes. For example, the current source may generate a high-frequency low-magnitude signal current. The electrodes for measuring an impedance cardiogram may be disposed around the neck and on the upper abdomen, for example. In the disclosure, like the electrocardiogram, the impedance cardiogram may be measured in a local region other than a large region where plural preset locations are separated, and this may be referred to as a local ICG (LICG).

Referring to FIG. 4. it illustrates DECG frequency components 410 and LICG frequency components 420 in a measured voltage response signal.

FIG. 5 illustrates a measured voltage response signal plotted on a time axis according to an embodiment of the disclosure.

Because the frequency components 410 of a DECG and the frequency components 420 of the LICG are different as shown in FIG. 4, when a band pass filter is used, the DECG and the LICG can be separated.

Part (a) of FIG. 5 illustrates a DECG, which may be similar to an electrocardiogram measured at plural preset locations. Part (b) of FIG. 5 illustrates the LICG.

It is possible to calculate the pulse arrival time (PAT) by using an electrocardiogram and impedance cardiogram being in synchronization. The PAT is a time duration from the time when the ventricle is depolarized to the time when the corresponding signal reaches the electrode, and may correspond to the difference between the time of the lowest point 510 of the Q wave of the differential electrocardiogram and the time of the lowest point 520 of the local impedance cardiogram. The PAT may be a value obtained by adding the pulse transit time (PTT) and the pulse ejection period (PEP). Here, the PTT may indicate the time taken for the pulse wave to travel between two arterial pulsation points, and the PEP may indicate the period in which the heart contracts to pump blood.

If the differential electrocardiogram and the local impedance cardiogram are measured using separate electrodes, synchronization between the two signals may be problematic. However, as the electronic device (e.g., the electronic device 101 in FIG. 1) according to various embodiments of the disclosure measures the differential electrocardiogram and the local impedance cardiogram by using a pair of electrodes, the two signals may be synchronized.

It is possible to calculate blood pressure (BP) by using the PAT or the PTT. Blood pressure includes systolic blood pressure (SBP) and diastolic blood pressure (DBP). SBP may be calculated by using Equation 11 and any one of Equations 1 to 10 below.

$SBP = a*\ln(PTT) + b$  Equation 1

$SBP = a*PTT^{-1} + b$  Equation 2

$SBP = a*PTT + b$  Equation 3

$SBP = a*PTT^2 + b*PTT + c$  Equation 4

$SBP = a*PTT^2 + b$  Equation 5

$SBP = a*e^{b*PTT}$  Equation 6

$SBP = a*PTT^{-2} + b$  Equation 7

$SBP = a*PTT^{-2} + b*HR^{-2} + c$  Equation 8

$SBP = a*\ln(PTT) + b*\ln(HR) + c$  Equation 9

$SBP = a*PTT + b*HR + c$  Equation 10

$PTT = PAT - PEP$  Equation 11

Here, HR (heart rate) indicates the heart rate, which is the number of times the heart beats for 1 minute, and a, b and c may be a specific constant.

The electronic device 101 can calculate systolic blood pressure by using Equations 1 to 6 without information on the HR, but may have to separately measure or calculate the heart rate to use Equations 7 to 10.

DBP can be calculated by using systolic blood pressure. The relationship between diastolic blood pressure and systolic blood pressure may be linear. For example, the slope of systolic blood pressure versus diastolic blood pressure may be 0.74±0.14.

Figure 6:
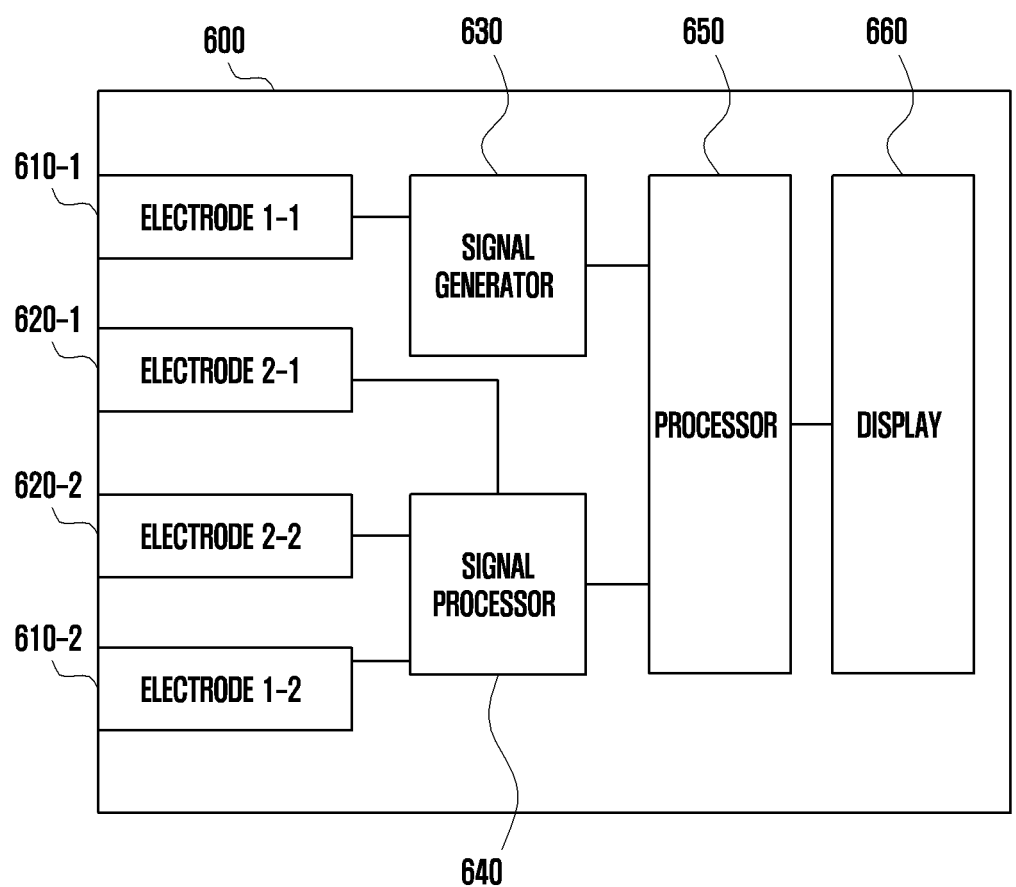
FIG. 6 is a block diagram of an electronic device according to an embodiment of the disclosure.

FIG. 6 is a block diagram of an electronic device according to an embodiment of the disclosure.

Referring to FIG. 6, according to various embodiments of the disclosure, the electronic device 600 (e.g., the electronic device 101 in FIG. 1) may include a plurality of electrodes 610-1, 610-2, 620-1 and 620-2 (e.g., the plural electrodes 210-1, 210-2, 220-1 and 220-2 in FIG. 2), a signal generator 630 (e.g., the signal generation module 220 in FIG. 2), a signal processor 640 (e.g., the signal measurement module 230 in FIG. 2), a processor 650 (e.g., the processor 120 in FIG. 1), and/or a display 660 (e.g., the display device 160 in FIG. 1).

According to various embodiments of the disclosure, the plural electrodes 610-1, 610-2, 620-1 and 620-2 may be configured as a part of the electronic device 600 or may be configured separately from the electronic device 600. For example, as described with reference to FIG. 2, the plural electrodes 610-1, 610-2, 620-1 and 620-2 may be placed on the electronic device 600 so as to be parallel or perpendicular to an artery. The size of the electrodes may also be determined based on the locations where the electrodes are disposed.

According to various embodiments of the disclosure, among first electrodes 610-1 and 610-2 (referred to as electrode 1-1 and electrode 1-2) of the plural electrodes, electrode 1-2 (610-2) may perform a function of reference matching by electrically connecting the user's body and the electronic device 600. For example, electrode 1-2 (610-2) may connect the ground of the electronic device 600 to the ground of the body. Electrode 1-2 (610-2) may perform a grounding function of the electronic device 600, and thus may become a reference for a voltage generated by the signal generator 630. In various embodiments of the disclosure, among the first electrodes 610-1 and 610-2 of the plural electrodes, electrode 1-1 (610-1) may transmit a signal generated by the signal generator 630 to the body.

According to various embodiments of the disclosure, the electronic device 600 may measure a voltage response signal by using second electrodes 620-1 and 620-2 (referred to as electrode 2-1 and electrode 2-2) among the plural electrodes. The measured voltage response signal may include both a local impedance cardiogram and a differential electrocardiogram. The distinction between the local impedance cardiogram and the differential electrocardiogram has been described with reference to FIGS. 4 and 5, and a description thereof may be omitted herein.

The signal generator 630 (e.g., the signal generation module 220 in FIG. 2) may generate a signal to measure a local impedance cardiogram. For example, the signal generator 630 may receive information on a signal to be generated from the processor 650, generate a signal, and transmit the signal to electrode 1-1 (610-1). The signal generated by the signal generator 630 may be a current signal.

The signal processor 640 (e.g., the signal measurement module 230 in FIG. 2) may process signals received from. For example, the signal received from electrode 1-2 (610-2), electrode 2-1 (620-1), and/or electrode 2-2 (620-2) may be measured as a voltage. The signal received from electrode 2-1 (620-1) and electrode 2-2 (620-2) may be a voltage response signal, and the signal received from electrode 1-2 (610-2) may be a reference signal. The reference signal is a signal that serves as a reference for a signal to be generated by the electronic device 600 using the signal generator 630 and may be a reference voltage. The signal processor 640 may detect a local impedance cardiogram and a differential electrocardiogram from the voltage response signal. The signal processor 640 may transmit the detected local impedance cardiogram and differential electrocardiogram to the processor 650.

The processor 650 may calculate the pulse arrival time by using the signal received from the signal processor 640, for example, a local impedance cardiogram and a differential electrocardiogram. The processor 650 may calculate blood pressure by using the pulse arrival time.

The display 660 may display information on blood pressure transmitted by the processor 650. For example, the display 660 may display both systolic blood pressure and diastolic blood pressure, and may indicate whether they are in the normal range by using a color. The display 660 may display blood pressure being updated in real time, or may display blood pressure in response to a user input.

Figure 7:
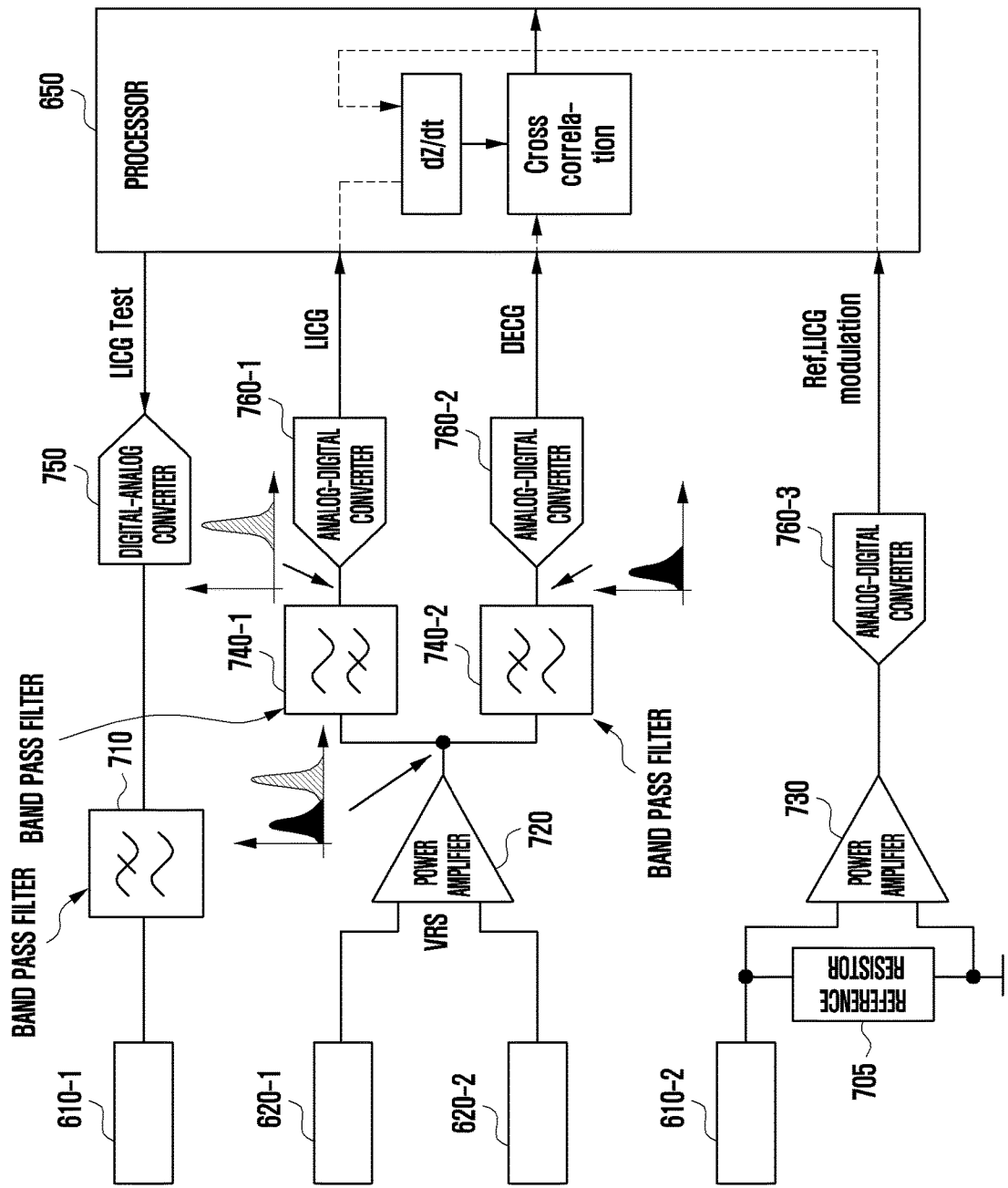
FIG. 7 is a block diagram of an electronic device according to an embodiment of the disclosure.

FIG. 7 is a block diagram of an electronic device according to an embodiment of the disclosure.

Referring to FIG. 7, according to various embodiments of the disclosure, the electronic device (e.g., the electronic device 600 in FIG. 6) may include a plurality of electrodes 610-1, 610-2, 620-1 and 620-2, a processor 650, a plurality of band pass filters 710, 740-1 and 740-2, a plurality of power amplifiers 720 and 730, a reference resistor 705, a digital-analog converter (DAC) 750, and a plurality of analog-digital converters (ADCs) 760-1, 760-2 and 760-3.

According to various embodiments of the disclosure, the plurality of electrodes 610-1, 610-2, 620-1 and 620-2 may be used for transmitting a generated signal to the body (electrode 610-1), connecting grounds of the body and the electronic device (electrode 610-2), or measuring a differential signal (electrodes 620-1 and 620-2).

According to various embodiments of the disclosure, the electronic device 600 may generate a signal for measuring a local impedance cardiogram and transmit it to the body. For example, the processor 650 of the electronic device 600 may transmit information on a signal to be generated as a digital signal to the digital-analog converter 750. The digital-analog converter 750 may generate an analog signal based on the received information. As the generated analog signal may contain noise, it may be processed by the band pass filter 710 and then transmitted to the body through the electrode 610-1.

Because the generated analog signal is not used within the electronic device 600 but is transmitted to the body outside the electronic device 600, a reference voltage may be required with respect to the body. Or, a reference voltage may be required to use the detected local impedance cardiogram. The electronic device 600 may measure a body voltage, for example a reference voltage, by using the electrode 610-2. The electrode 610-2 is connected to the reference resistor 705 and the power amplifier 730, so that the measured body voltage can be amplified in magnitude. The measured body voltage may be a difference from the reference voltage of the electronic device 600. The amplified signal may be input to the analog-digital converter 760-3 and converted into a digital signal, which may then be input to the processor 650. According to various embodiments of the disclosure, the processor 650 may generate a signal with respect to the measured body voltage, and may analyze measured signals.

According to various embodiments of the disclosure, as described above, the electronic device 600 may measure a voltage response signal by using a pair of electrodes 620-1 and 620-2. The magnitude of the measured voltage response signal may be amplified by the power amplifier (PA) 720. The measured voltage response signal may include a differential electrocardiogram and a local impedance cardiogram. As the differential electrocardiogram and the local impedance cardiogram have different frequency bands, they may be detected by using the different band pass filters 740-1 and 740-2.

The band pass filter 740-1 corresponding to the frequency of the local impedance cardiogram may be applied to the measured voltage response signal, and the output signal may be converted into a digital signal by using the analog-digital converter 760-1. The local impedance cardiogram converted into a digital signal may be input to the processor 650 for calculating the pulse arrival time and blood pressure. As the local impedance cardiogram is a measurement of a body's response to a signal generated by the electronic device 600, it may be used together with a reference voltage measured by the electrode 610-2.

The band pass filter 740-2 corresponding to the frequency of the differential electrocardiogram may be applied to the measured voltage response signal, and the output signal may be converted into a digital signal by using the analog-digital converter 760-2. The differential electrocardiogram converted into a digital signal may also be input to the processor 650 for calculating the pulse arrival time and blood pressure.

The processor 650 may differentiate the local impedance cardiogram corresponding to, for example, the reference voltage, and calculate the pulse arrival time based on a correlation between the differentiated local impedance cardiogram and the differential electrocardiogram. The processor 650 may calculate blood pressure (e.g., systolic blood pressure) by using the pulse arrival time and one of Equations 1 to 10 listed above.

Figure 8:
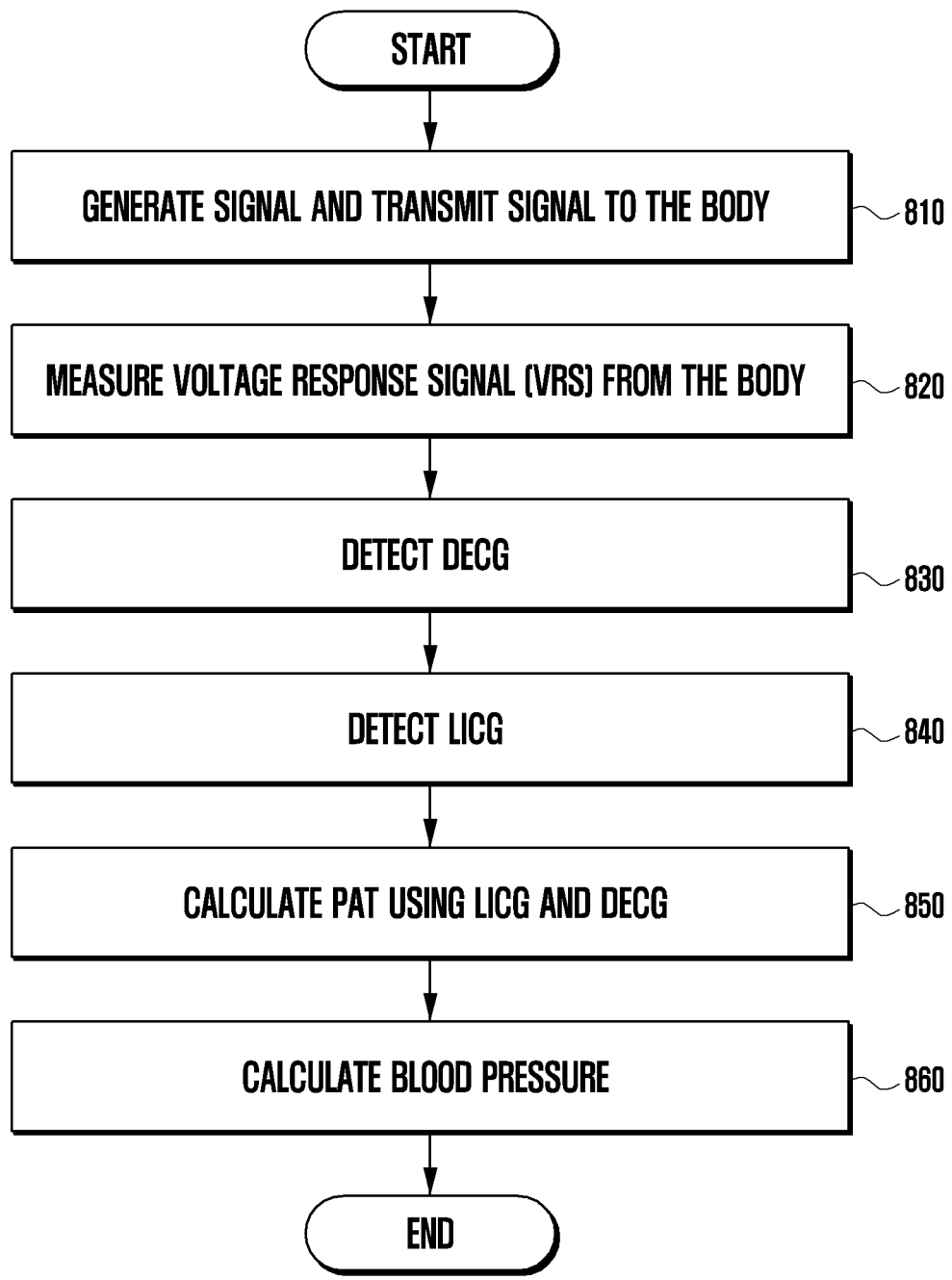
FIG. 8 is a flowchart of a method for an electronic device according to an embodiment of the disclosure.

FIG. 8 is a flowchart of a method for an electronic device according to an embodiment of the disclosure.

Referring to FIG. 8, according to various embodiments of the disclosure, at operation 810, the signal generator (e.g., the signal generator 630 in FIG. 6) of the electronic device (e.g., the electronic device 600 in FIG. 6) may generate a signal and transmit the signal to the body. A plurality of electrodes (e.g., the first electrodes 610-1 and 610-2 in FIG. 6) may be used to transmit the generated signal. The signal generator 630 may generate a current and may generate a signal (e.g., a current) having a specific frequency.

At operation 820, the electronic device 600 may measure a voltage response signal (VRS) from the body by using plural electrodes (e.g., the second electrodes 620-1 and 620-2 in FIG. 6). For example, the plural electrodes 620-1 and 620-2 may be a pair of electrodes, and may be placed parallel or perpendicular to an artery. The plural electrodes 620-1 and 620-2 may be disposed at a location close to the plural electrodes 610-1 and 610-2 used to transmit the generated signal, and may be configured as a part of the electronic device 600 or may be configured separately. The electronic device 600 may measure the voltage response signal with a sampling frequency higher than the frequency of the signal generated by the signal generator 630.

At operation 830, the electronic device 600 may detect a DECG from the measured VRS. The differential electrocardiogram may indicate an electrocardiogram measured at one local location on the body other than an electrocardiogram measured at plural designated locations on the body, and may be measured on, for example, the wrist, leg, arm, nose, or face. As the differential electrocardiogram has a frequency of 0.3 to 35 Hz, the electronic device 600 may detect a differential electrocardiogram from the voltage response signal by using a band pass filter (e.g., the band pass filter 740-2 in FIG. 7).

At operation 840, the electronic device 600 may detect the LICG from the measured voltage response signal. The local impedance cardiogram may indicate an impedance cardiogram measured at one local location on the body other than an impedance cardiogram measured at plural designated locations on the body. Like a differential electrocardiogram, the local impedance cardiogram may be measured on, for example, the wrist, leg, arm, nose, or face. According to various embodiments of the disclosure, the frequency of the local impedance cardiogram may be similar to the frequency of the signal generated by the signal generator 630 of the electronic device 600, and the frequency bandwidth may be 50 Hz. The electronic device 600 may detect a local impedance cardiogram from the voltage response signal by using a band pass filter (e.g., the band pass filter 740-1 in FIG. 7).

At operation 850, the electronic device 600 may calculate the PAT by using the detected DECG and LICG. The PAT may be a time difference between the lowest point (e.g., the point 510 in FIG. 5) of the Q wave of the differential electrocardiogram and the lowest point (e.g., the point 520 in FIG. 5) of the local impedance cardiogram.

At operation 860, the electronic device 600 may calculate blood pressure based on the PAT. The electronic device 600 may calculate systolic blood pressure by using some of Equations 1 to 11. In addition, the electronic device 600 may use systolic blood pressure to calculate diastolic blood pressure being in a proportional relationship therewith.

According to various embodiments of the disclosure, the electronic device 600 may notify measured blood pressure to the user. For example, the electronic device 600 may use an application to notify measured blood pressure to the user. In various embodiments of the disclosure, the electronic device 600 may receive measured blood pressure and display it to the user.

Figure 9:
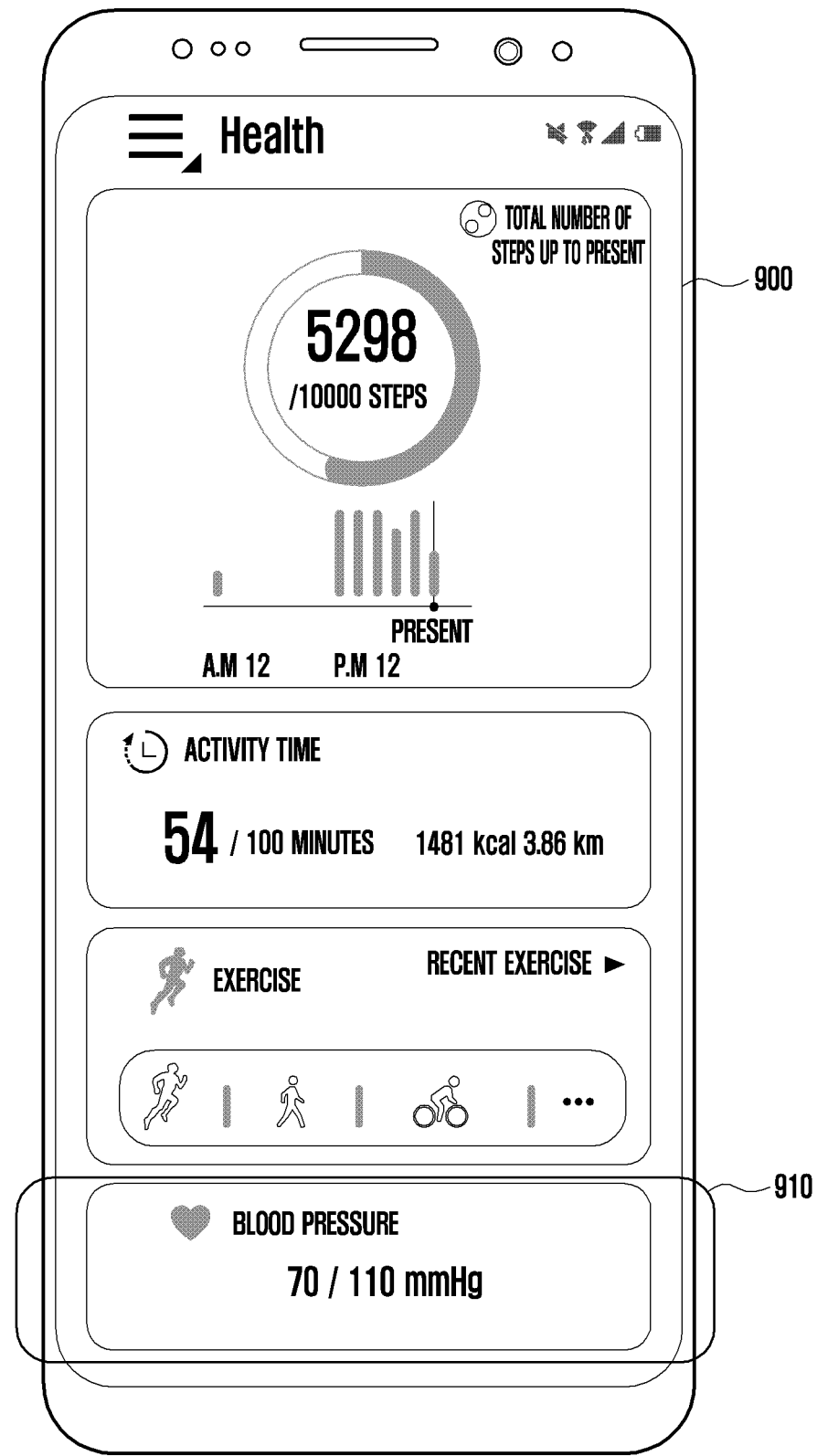
FIG. 9 illustrates a partial screen of an application running on an electronic device according to an embodiment of the disclosure.

FIG. 9 illustrates a partial screen of an application running on an electronic device according to an embodiment of the disclosure.

Referring to FIG. 9, a screen 900 illustrates measured blood pressure as a portion of output information produced by an application that provides health-related information of the user.

Referring to FIG. 9, the application may provide the user's health-related information, such as the number of operations taken up to the present, activity time, exercise amount, and blood pressure. The blood pressure value 910 provided through the application may be a blood pressure value measured in real time from the user. When a normal range of blood pressure is set, the electronic device (e.g., the electronic device 600 in FIG. 6) may generate an alarm if the measured blood pressure value is out of the normal range. Such an alarm may be at least one of vibration, sound, or notification on the screen. Depending on user settings, the alarm may be transmitted to another user's electronic device or a related medical institution. In FIG. 9, the blood pressure value 910 provided by the application indicates both systolic blood pressure and diastolic blood pressure, but the user may configure settings to display only one of systolic blood pressure and diastolic blood pressure.

According to various embodiments of the disclosure, the user may execute a specific application to measure blood pressure through the electronic device. According to various embodiments of the disclosure, the application for measuring blood pressure may be an application that is always executed on the electronic device.

According to various embodiments of the disclosure, an electronic device may include at least two pairs of electrodes, and a processor, wherein the processor may be configured to generate a signal and output the signal by using one pair of electrodes, measure a voltage response signal by using another pair of electrodes, detect a differential electrocardiogram from the measured voltage response signal, detect a local impedance cardiogram from the measured voltage response signal, calculate a pulse arrival time by using the detected differential electrocardiogram and local impedance cardiogram, and calculate blood pressure by using the calculated pulse arrival time.

In the electronic device according to various embodiments of the disclosure, the two pairs of electrodes may be disposed perpendicular to an artery.

In the electronic device according to various embodiments of the disclosure, the plural electrodes may be disposed parallel to an artery.

In the electronic device according to various embodiments of the disclosure, the signal output by using the pair of electrodes may be a current.

In the electronic device according to various embodiments of the disclosure, the calculated blood pressure may be systolic blood pressure and diastolic blood pressure.

In the electronic device according to various embodiments of the disclosure, the blood pressure may be calculated by further using the heart rate.

In the electronic device according to various embodiments of the disclosure, the detected differential electrocardiogram and the detected local impedance cardiogram may be synchronized signals.

In the electronic device according to various embodiments of the disclosure, the processor may be configured to detect the differential electrocardiogram by using a band pass filter.

In the electronic device according to various embodiments of the disclosure, the processor may be configured to detect the local impedance cardiogram by using a band pass filter.

According to various embodiments of the disclosure, the electronic device may further include a display to display information on the calculated blood pressure.

According to various embodiments of the disclosure, a method of operating an electronic device may include generating a signal and outputting the signal by using one pair of electrodes, measuring a voltage response signal by using another pair of electrodes, detecting a differential electrocardiogram from the measured voltage response signal, detecting a local impedance cardiogram from the measured voltage response signal, calculating a pulse arrival time by using the detected differential electrocardiogram and local impedance cardiogram, and calculating blood pressure by using the calculated pulse arrival time.

In the method of operating the electronic device according to various embodiments of the disclosure, the voltage response signal may be measured by using the pair of electrodes disposed perpendicular to an artery.

In the method of operating the electronic device according to various embodiments of the disclosure, the voltage response signal may be measured by using the pair of electrodes disposed parallel to an artery.

In the method of operating the electronic device according to various embodiments of the disclosure, the signal output by using the pair of electrodes may be a current.

In the method of operating the electronic device according to various embodiments of the disclosure, the calculated blood pressure may be systolic blood pressure and diastolic blood pressure.

In the method of operating the electronic device according to various embodiments of the disclosure, the blood pressure may be calculated by further using the heart rate.

In the operation method of operating the electronic device according to various embodiments of the, the detected differential electrocardiogram and the detected local impedance cardiogram may be synchronized signals.

In the method of operating the electronic device according to various embodiments of the disclosure, the detected differential electrocardiogram may be a signal detected by using a band pass filter.

In the method of operating the electronic device according to various embodiments of the disclosure, the detected local impedance cardiogram may be a signal detected by using a band pass filter.

According to various embodiments of the disclosure, the method of operating the electronic device may further include displaying information on the calculated blood pressure.

In addition, various other embodiments are possible.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 140) including one or more instructions that are stored in a storage medium (e.g., the internal memory 136 or the external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
    at least two pairs of electrodes; and
    a processor,
    wherein the processor is configured to:
        generate a signal and output the signal by using a first pair of electrodes of the at least two pairs of electrodes,
        measure a voltage response signal by using a second pair of electrodes of the at least two pairs of electrodes,
        detect a differential electrocardiogram from the measured voltage response signal,
        detect a local impedance cardiogram from the measured voltage response signal, the local impedance cardiogram measuring an impedance of a chest,
        calculate a pulse arrival time by using the detected differential electrocardiogram and the detected local impedance cardiogram, and
        calculate blood pressure by using the calculated pulse arrival time, and
    wherein the measured voltage response signal used to detect the local impedance cardiogram and the measured voltage response signal used to detect the differential electrocardiogram comprise the same measured voltage response signal detected by the same second pair of electrodes,
    wherein the electronic device further comprises:
        a first band pass filter configured to filter the measured voltage response signal in a first frequency band corresponding to the differential electrocardiogram, and
        a second band pass filter configured to filter the measured voltage response signal in a second frequency band corresponding to the local impedance cardiogram,
    wherein the detection of the differential electrocardiogram from the measured voltage response signal is performed by the processor using the first band pass filter, and
    wherein the detection of the local impedance cardiogram from the measured voltage response signal is performed by the processor using the second band pass filter.

2. The electronic device of claim 1, wherein the at least two pairs of electrodes are configured to be disposed perpendicularly to an artery.

3. The electronic device of claim 1, wherein the at least two pairs of electrodes are configured to be disposed parallel to an artery.

4. The electronic device of claim 1, wherein the signal which is output by using the first pair of electrodes includes a current.

5. The electronic device of claim 1, wherein the calculated blood pressure includes systolic blood pressure and diastolic blood pressure.

6. The electronic device of claim 1, wherein the blood pressure is calculated by further using a heart rate.

7. The electronic device of claim 1, wherein a signal of the detected differential electrocardiogram and a signal of the detected local impedance cardiogram are synchronized with each other.

8. The electronic device of claim 1, further comprising a display to display information on the calculated blood pressure.

9. The electronic device of claim 1, wherein the pulse arrival time corresponds to a difference between a time of a lowest point of a Q wave of the differential electrocardiogram and a time of a lowest point of the local impedance cardiogram.

10. A method of operating an electronic device, the method comprising:
    generating, using a processor of the electronic device, a signal and outputting the signal by using a first pair of electrodes;
    measuring, using the processor of the electronic device, a voltage response signal by using a second pair of electrodes;
    detecting a differential electrocardiogram from the measured voltage response signal, the detection of the differential electrocardiogram from the measured voltage response signal being performed by the processor of the electronic device using a first band pass filter configured to filter the measured voltage response signal in a first frequency band corresponding to the differential electrocardiogram;
    detecting a local impedance cardiogram from the measured voltage response signal, the local impedance cardiogram measuring an impedance of a chest, the detection of the local impedance cardiogram from the measured voltage response signal being performed by the processor of the electronic device using a second band pass filter configured to filter the measured voltage response signal in a second frequency band corresponding to the local impedance cardiogram;
    calculating, using the processor of the electronic device, a pulse arrival time by using the detected differential electrocardiogram and the detected local impedance cardiogram; and
    calculating, using the processor of the electronic device, blood pressure by using the calculated pulse arrival time,
    wherein the measured voltage response signal used to detect the local impedance cardiogram and the measured voltage response signal used to detect the differential electrocardiogram comprise the same measured voltage response signal detected by the same second pair of electrodes.

11. The method of claim 10, wherein the voltage response signal is measured by using the second pair of electrodes disposed perpendicular to an artery.

12. The method of claim 10, wherein the voltage response signal is measured by using the second pair of electrodes disposed parallel to an artery.

13. The method of claim 10, wherein the signal, which is outputted by the first pair of electrodes, includes a current.

14. The method of claim 10, wherein the calculated blood pressure includes systolic blood pressure and diastolic blood pressure.

15. The method of claim 10, wherein the blood pressure is calculated by further using a heart rate.

16. The method of claim 10, wherein a signal of the detected differential electrocardiogram and a signal of the detected local impedance cardiogram are synchronized with each other.

17. The method of claim 10, further comprising displaying information on the calculated blood pressure.

18. The method of claim 10, wherein the first pair of electrodes and the second pair of electrodes are included in at least one of a ring, a necklace, clothes, or a sock.

19. The method of claim 10, wherein the electronic device is included in at least one of a watch, an arm band, a wrist band, a leg band, or eyeglasses.

20. The method of claim 10,
  wherein the calculated pulse arrival time includes a time duration from a time when a ventricle is depolarized to a time when a corresponding signal reaches the first pair of electrodes and the second pair of electrodes, or
  wherein the calculated pulse arrival time includes a value obtained by adding a pulse transit time and a pulse ejection period.

* * * * *